(12) United States Patent
Chiu et al.

(10) Patent No.: US 12,318,160 B2
(45) Date of Patent: Jun. 3, 2025

(54) CONTROLLING SYSTEM AND CONTROLLING METHOD OF ENDOSCOPIC SURGICAL ROBOT BASED ON HEAD TRACKING

(71) Applicant: ISSA TECHNOLOGY CO., LTD., Taoyuan (TW)

(72) Inventors: Chi-Wei Chiu, Taoyuan (TW); Chih-Kun Huang, Taoyuan (TW)

(73) Assignee: ISSA TECHNOLOGY CO., LTD., Taoyuan (TW)

( * ) Notice: Subject to any disclaimer, the term of this patent is extended or adjusted under 35 U.S.C. 154(b) by 513 days.

(21) Appl. No.: 17/888,658

(22) Filed: Aug. 16, 2022

(65) Prior Publication Data
US 2023/0277263 A1 Sep. 7, 2023

(30) Foreign Application Priority Data
Mar. 1, 2022 (TW) .................................. 111107393

(51) Int. Cl.
*A61B 34/37* (2016.01)
(52) U.S. Cl.
CPC .................................. *A61B 34/37* (2016.02)
(58) Field of Classification Search
CPC .......... A61B 34/37; A61B 2017/00216; A61B 34/30; A61B 34/25; A61B 1/00006; A61B 1/00009; A61B 1/00039; A61B 1/00045; A61B 1/313; A61B 34/70; A61B 90/361; G06F 3/012
See application file for complete search history.

(56) References Cited

U.S. PATENT DOCUMENTS

| | | | |
|---|---|---|---|
| 2021/0030498 A1* | 2/2021 | Peine | A61B 34/76 |
| 2023/0010350 A1* | 1/2023 | Peine | A61B 90/06 |
| 2023/0083605 A1* | 3/2023 | Robinson | G06V 40/107 606/1 |
| 2023/0329818 A1* | 10/2023 | Hares | A61B 34/20 |
| 2024/0390089 A1* | 11/2024 | Kobayashi | A61B 34/30 |

* cited by examiner

*Primary Examiner* — Iriana Cruz
(74) *Attorney, Agent, or Firm* — Chun-Ming Shih; HDLS IPR SERVICES (57) ABSTRACT

A controlling system of an endoscopic surgical robot based on head tracking is disclosed. The system includes a host, the robot and a complex camera. The robot holds an endoscope at a specific position through a specific gesture. The complex camera includes a 2D camera for obtaining facial features of a doctor to identify whether the doctor is a registered user. The complex camera includes a 3D camera for obtaining depth information of the doctor's head. The host estimates a 2D space information and a 3D space information of the doctor's head according to the facial features and the depth information, and transforms the 2D space information and 3D space information to a robot moving information by a transformation matrix to control the robot to move.

15 Claims, 8 Drawing Sheets

CONTROLLING SYSTEM AND CONTROLLING METHOD OF ENDOSCOPIC SURGICAL ROBOT BASED ON HEAD TRACKING

BACKGROUND OF THE DISCLOSURE

Technical Field

The disclosure relates to a controlling system and a controlling method of a robot, particularly relates to a controlling system and a controlling method for controlling a robot used in an endoscopic surgery.

Description of Related Art

In the present endoscopic surgery (for example, laparoscopic operation), the operating surgeon needs to control the related instruments to perform operation by two hands, and the endoscope is held through the assistance from the physician assistant to obtain the image in the patient's body.

During the endoscopic surgery, the endoscope is held by the physician assistant, and the physician assistant is instructed by the surgeon to operate the endoscope (for example, rotating the camera, moving left, moving right, zoom in, zoom out, etc.).

Figure 1:
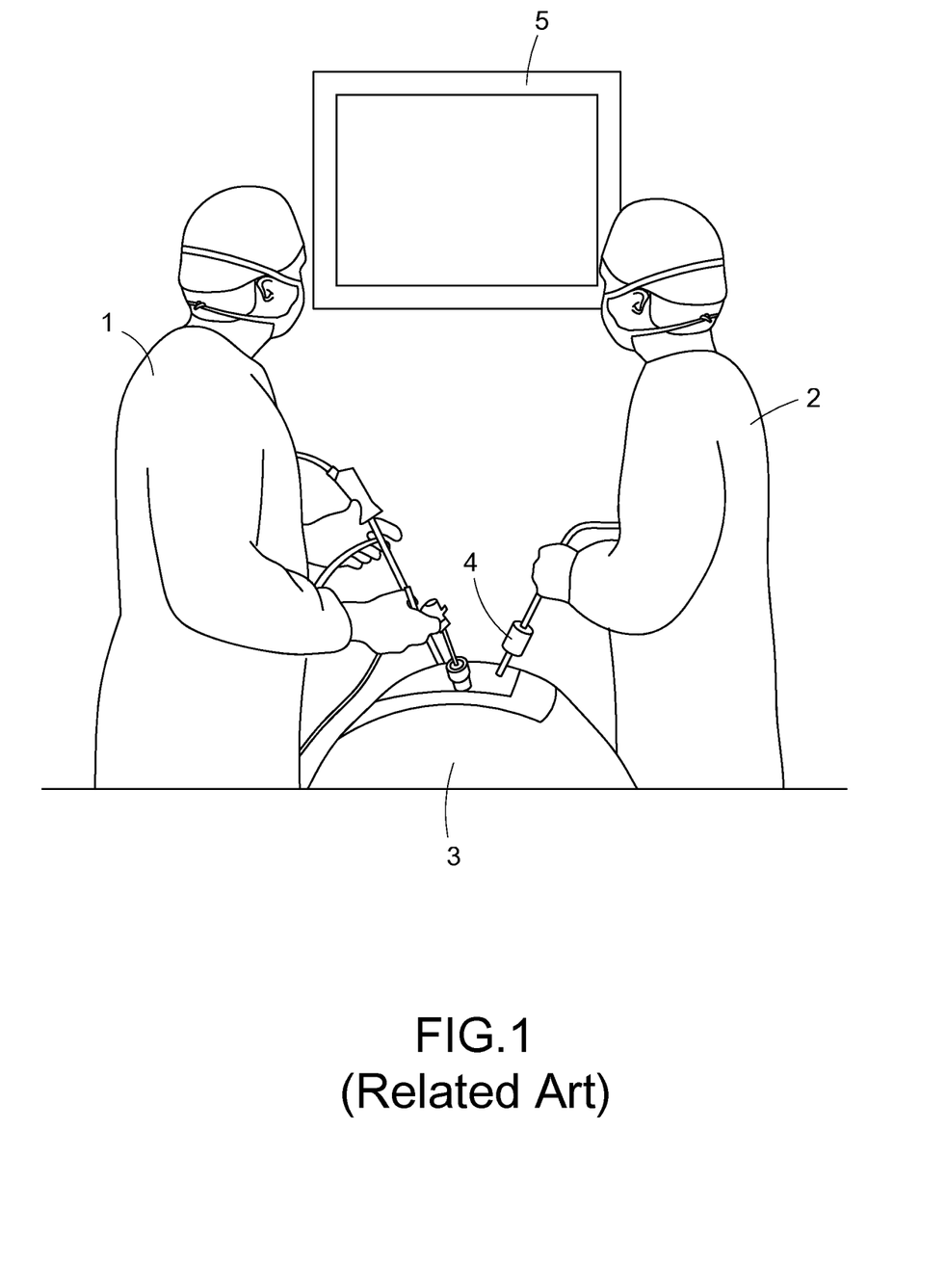
FIG. 1 is a schematic diagram of the scenario of performing the endoscopic surgery.

Please refer to FIG. 1, which is a schematic diagram of the scenario of performing the endoscopic surgery. As shown in FIG. 1, in the operating room, the surgeon 1 uses the related instruments by two hands, and the physician assistant 2 holds and operates the endoscope 4 inserted into the patient's body. Further, the image taken by the endoscope 4 is displayed on the display screen 5 on one side of the operating room. As a result, the surgeon may check related image on the display screen 5 to operate the instruments on the hands to perform operation.

However, the physician assistant 2 needs to operate the endoscope 4 by the surgeon's view to make the endoscope 4 capture the image which the surgeon really needs. In order to effectively and precisely operate the endoscope 4, the surgeon 1 and physician assistant 2 need long-term communication and training to achieve desirable tacit understanding.

As described above, the physician assistant 2 generally needs long-term training and the cost of the training is relatively high, and searching and cultivating of the talent are a difficult matter. Further, the physician assistant 2 needs to keep the same gesture for a long period of time during the operation to maintain the stability of the endoscope 4, thereby easily feeling weary in the operation of many hours. As a result, that may cause the image to shake and increase risk of the operation.

In view of this, the inventors have devoted themselves to the aforementioned related art, researched intensively try to solve the aforementioned problems.

SUMMARY OF THE DISCLOSURE

The disclosure provides a controlling system and a controlling method controlling an endoscopic surgical robot based on head tracking, which the doctor (or surgeon) in the operation may directly control the robot's movement through head's minor action to adjust the angle of view (AOV) of the endoscope correspondingly.

In some embodiments of the disclosure, a controlling system is configured to control an endoscopic surgical robot based on head tracking and applied in an operating room. The controlling system includes:
 a host;
 a robot, connected with the host and configured to hold an endoscope used in the operating room at a specific position by a specific gesture; and
 a complex camera, including a 2D camera and a 3D camera, the 2D camera configured to obtain a facial feature (or any feature uncovered by the mask) of a doctor in the operating room, and the 3D camera configured to obtain a depth information of the doctor's head, wherein the 2D camera and the 3D camera achieve an RGB-D registration through pre-alignment;
 wherein the host is configured to identify the facial feature to determine whether the doctor is a registered user, and compare the depth information to the facial feature to determine whether the facial feature and the depth information are both consistent with the registered user, when the doctor is determined to be the registered user and the facial feature and the depth information are determined to be consistent with the registered user, the host is configured to estimate a 2D space information and a 3D space information of the doctor's head according to the facial feature and the depth information, transform the 2D space information and the 3D space information to a robot moving information by a transformation matrix, and control the robot to move according to the robot moving information.

In some embodiments of the disclosure, a controlling method is used to control an endoscopic surgical robot based on head tracking, applied to a controlling system including a robot, a complex camera and a host. The controlling method includes:
 a) controlling the robot to hold an endoscope used in an operating room at a specific position by a specific gesture;
 b) obtaining, by a 2D camera in the complex camera, a facial feature of a doctor in the operating room;
 c) identifying, by the host, the facial feature to determine whether the doctor is a registered user;
 d) obtaining, by a 3D camera in the complex camera, a depth information of the doctor's head, wherein the 2D camera and the 3D camera achieve an RGB-D registration through pre-alignment;
 e) comparing, by the host, the depth information to the facial feature to determine whether the facial feature and the depth information are both consistent with the registered user;
 f) when the doctor is determined to be the registered user and the facial feature and the depth information are determined to be consistent with the registered user, estimating, by the host, a 2D space information and a 3D space information of the doctor's head according to the facial feature and the depth information;
 g) transforming, by the host, the 2D space information and the 3D space information to a robot moving information by a transformation matrix; and
 h) controlling, by the host, the robot to move according to the robot moving information.

The disclosure uses the robot to hold (or grip) the endoscope, and uses the camera to track action of the doctor's head. The robot's movement is directly controlled according to action of the doctor's head to adjust AOV of the endoscope. Comparing to the related art, the disclosure may reduce the reliance to manpower, such as the physician assistant, in the operation, and make the control of the endoscope be intuitive for the doctor.

DETAILED DESCRIPTION

The technical contents of this disclosure will become apparent with the detailed description of embodiments accompanied with the illustration of related drawings as follows. It is intended that the embodiments and drawings disclosed herein are to be considered illustrative rather than restrictive.

Figure 2:
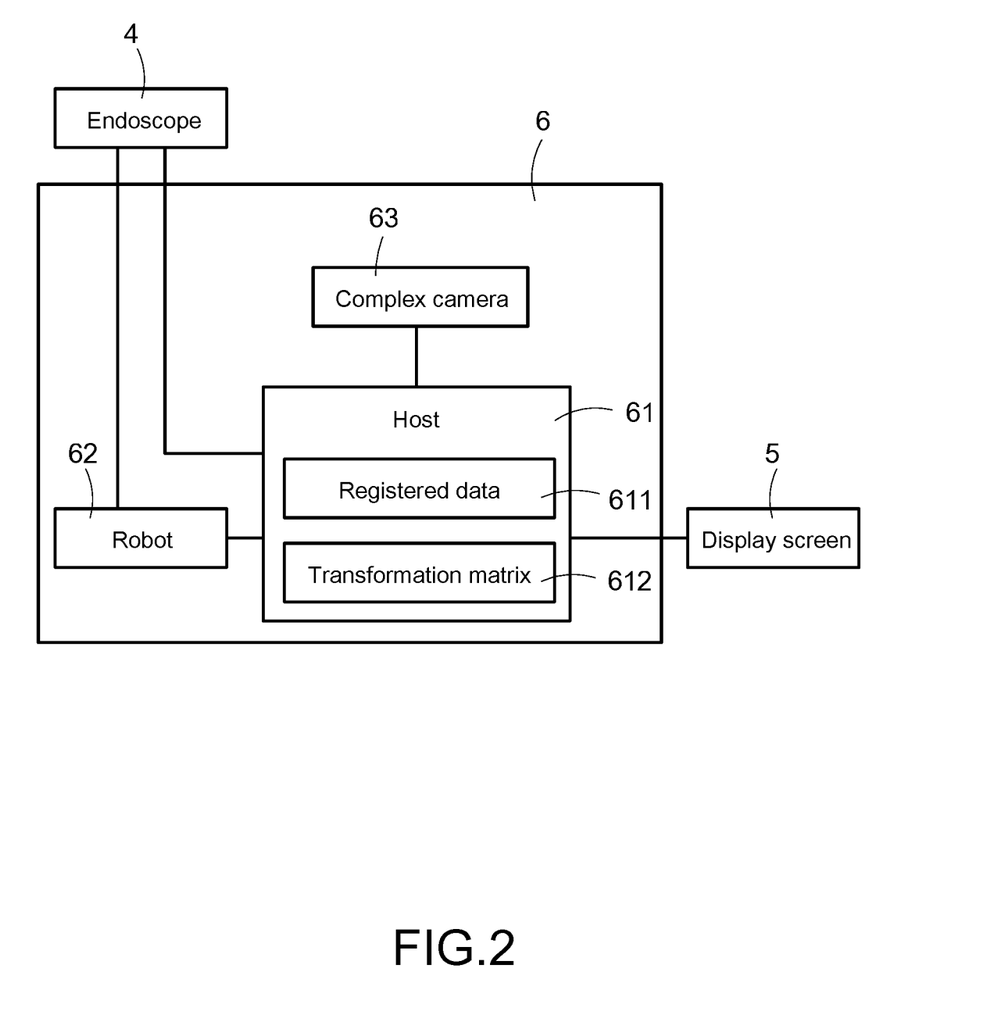
FIG. 2 is a block diagram of the controlling system in accordance with the first embodiment of the disclosure.
Figure 3:
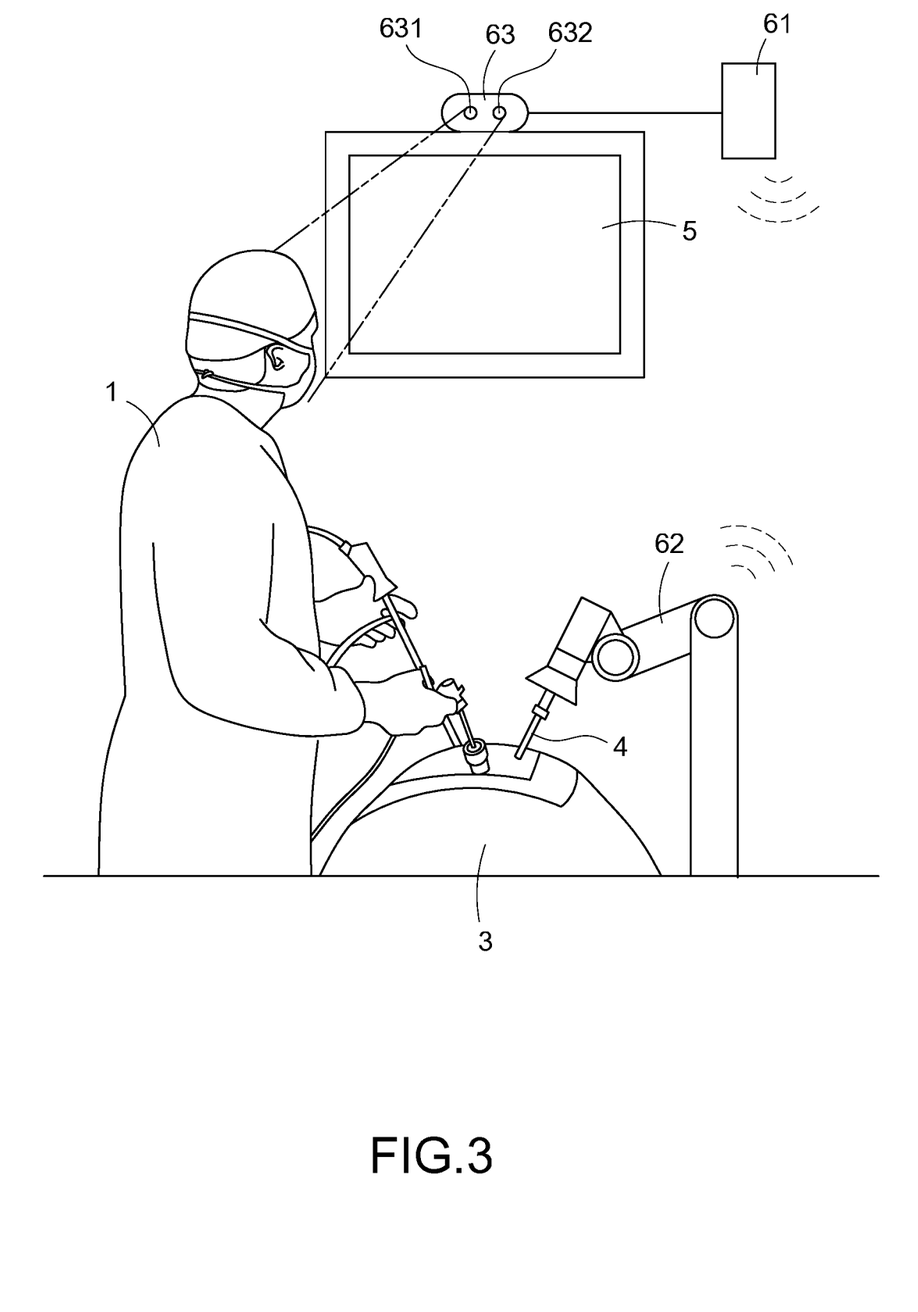
FIG. 3 is a schematic diagram of the scenario of performing the endoscopic surgery in accordance with the first embodiment of the disclosure.

Please refer to FIG. 2 and FIG. 3, FIG. 2 is a block diagram of the controlling system in accordance with the first embodiment of the disclosure, FIG. 3 is a schematic diagram of the scenario of performing the endoscopic surgery in accordance with the first embodiment of the disclosure.

The disclosure discloses a controlling system configured to control an endoscopic surgical robot based on head tracking (abbreviated as the controlling system 6 hereafter in the specification). As shown in FIG. 2, the controlling system 6 at least includes a host 61, a robot 62 and a complex camera 63. The host 61, robot 62 and complex camera 63 are communicatively connected.

As shown in FIG. 3, the controlling system 6 of the disclosure is mainly applied in the operating room. The robot 62 is used to hold (or grip) the endoscope 4 used by the doctor (or surgeon) 1 in the operating room. The complex camera 63 is used to detect and track the action of the operating doctor's head. The host 61 is configured to control the robot 62 based on the detecting and tracking result of the complex camera 63. The endoscope 4 is held by the robot 62, and thus when the robot 62 is controlled by the host 61 to move, the endoscope 4 gripped by the robot 62 may jointly perform actions such as move, rotate, zoom in, and zoom out, etc., to further adjust AOV of the endoscope 4.

In some embodiments, the host 61 is connected to the endoscope 4 and the display screen 5 arranged on one side of the operating room. The endoscope 4 is inserted into the patient's body during the operation and configured to continuously detect the image in the patient's body. The host 61 is configured to receive the image detected by the endoscope 4 and transmit that to the display screen 5 to display. Therefore, the doctor 1 may acquire related information in the patient's body according to the image displayed on the display screen 5 to perform the operation.

In some other embodiments, the host may be configured to perform image processing to the image (for example, gamma correction, color correction, edge enhancement, etc.), after received the image detected by the endoscope 4, to optimize the image, and transmit that to the display screen 5 to display. Therefore, the doctor 1 may acquire more details from the image displayed on the display screen 5. The aforementioned description is part of the embodiments of the disclosure, here is not intended to be limiting.

In some other embodiments, the endoscope 4 may be directly connected to the display screen 5, and directly output the detected image to the display screen 5 to display without being connected to the host 61.

It is worth mentioning that, in some embodiments, the host 61 and robot 62 may be communicatively connected with each other in a wired manner or a wireless manner, and the robot 62 holds the endoscope 4 through a fixed structure. That is, the host 61 does not directly control the endoscope 4. In some embodiments, the host 61 is configured to control the robot 62 to move according to the detecting and tracking result of the complex camera 63. When the robot 62 moves, the endoscope 4 held by the robot 62 moves correspondingly to change AOV of the endoscope 4.

In some other embodiments, the endoscope 4 is the modified endoscope with communication function. The host 61 and endoscope 4 may be communicatively connected with each other in a wired manner or a wireless manner. In some embodiments, the robot 62 is only used for holding and keeping the endoscope 4 in stable, and the robot 62 is not directly connected to the host 61. The host 61 is configured to directly control the endoscope 4 to move according to the detecting and tracking result of the complex camera 63 to adjust AOV of the endoscope 4 and obtain required image.

The aforementioned description is part of the embodiments of the disclosure, here is not intended to be limiting.

As shown in FIG. 3, the complex camera 63 of the disclosure mainly includes a 2D camera 631 and a 3D camera 632. The 2D camera 631 may be, for example, a color camera. The 3D camera 632 may be, for example, a LiDAR camera. Specifically, in the disclosure, the 2D camera 631 is the camera which supports RGB color photography, and the 3D camera 632 is the camera which detects external image and generates the depth information through time-of-flight (ToF) technology, stereoscopy technology or structure light technology, here is not intended to be limiting.

In the embodiment of FIG. 2 and FIG. 3, the 2D camera 631 and 3D camera 632 are jointly disposed on the single complex camera 63. In some other embodiments, the 2D camera 631 and 3D camera 632 may be disposed separately for two independent devices, and is not limited to the embodiment shown in FIG. 2 and FIG. 3. For better understanding, here uses the complex camera 63 having the 2D camera 631 and 3D camera 632 as an example to explain, here is not intended to be limiting.

As shown in FIG. 3, the image captured by the endoscope 4 is displayed on the display screen 5, and the complex camera 63 (that is, the 2D camera 631 and 3D camera 632) is disposed above the display screen 5. When the doctor 1 looks up to check the display screen 5 during the operation, the complex camera 63 may capture and track features such as moving, rotating, or swinging, etc., of the doctor 1's head (including face and eye). The host 61 is configured to control the robot 62 to move correspondingly according to the features to further drive the endoscope 4 through the robot 62 to move toward the moving direction of the doctor 1's head.

The disclosure is used to make the endoscope 4 move based on the actions of the doctor 1's head and adjust AOV of the endoscope 4 according to the doctor 1's view. Therefore, the endoscope 4 may perform shooting in the patient 3's body based on the doctor 1's view. As a result, the endoscope 4 may effectively obtain the image, which the doctor 1 truly needs, without over-assistance from the physician assistant.

Before the operation, the doctor 1 or the physician assistant still needs to operate the robot 62 manually to make the robot 62 hold the endoscope 4 at the specific position by the specific gesture. Specifically, the doctor 1 or the physician assistant needs to insert the endoscope 4 into the patient 3's body and locate the endoscope 4 at the specific position in the patient 3's body. At the same time, the doctor 1 or the physician assistant may operate the robot 62 to hold the endoscope 4 positioned at the specific position. When the robot 62 stably holds the endoscope 4 to replace the physician assistant, the physician assistant may leave, and the doctor 1 may fully control the endoscope 4 (that is, the doctor 1 fully controls the robot 62).

Therefore, the robot 62 replace the character of the physician assistant in the related art, that is holding the endoscope 4 during the whole operation and operating the endoscope 4 according to the doctor 1's instruction. Afterward, the doctor 1 may control the robot 62 by head's movement through the controlling system 6 of the disclosure, and further partly control (for example, rotating camera, finely adjusting position, etc.) the endoscope 4 held by the robot 62.

After the robot 62 and endoscope 4 are arranged, the controlling system 6 of the disclosure is configured to capture the facial feature (or any feature uncovered by the mask) of the doctor 1 through the 2D camera 631, and capture the depth information of the doctor 1's head through the 3D camera 632. Further, the host 61 is configured to identify the doctor 1's identity through the facial feature and depth information, and track the actions of the doctor 1's head to control the movement of the robot 62.

Specifically, the host 61 is configured to identify the facial feature obtained by the 2D camera 631 in advance to perform primary recognition stage and determine whether the doctor 1 is a registered user. If the doctor 1 is determined to be the registered user, the controlling system 6 is configured to accept the control from the doctor 1.

Specifically, the host 61 of the disclosure may be a computer host having a deep learning accelerator (DLA) or a graphics processing unit (GPU). The controlling system 6 of the disclosure needs to capture the facial features of one or multiple doctors, that are authorized to use the controlling system 6, through the complex camera 63 or the other image capturing devices (not shown in figures) in advance, and record those to be the registered data 611 through the deep learning algorithm in the host 61. As shown in FIG. 2, the host 61 of the disclosure is configured to store multiple registered data 611, and the multiple registered data 611 respectively record the facial features of different registered users. When identifying the doctor 1's identity, the host 61 is configured to compare the obtained facial feature with the multiple registered data 611 to identify whether the doctor 1 is one of the registered users.

When the doctor 1 is determined to be the registered user and the doctor 1's identity is confirmed, the host 61 is configured to further obtain the depth information through the 3D camera 632 to perform a secondary confirmation stage.

As described above, the technical feature of the disclosure is tracking the actions of the doctor 1's head, face or eye to control the robot 62 correspondingly. When the image tracking technology is applied to non-formal application scenarios such as game or audio-visual entertainment, the system may accept wider deviation. Comparing to that, the controlling system 6 of the disclosure is applied to high-risk operating room, subtle and precise identification, tracking and control are necessary. The disclosure combines the facial feature captured by the 2D camera 631 and the depth information obtained by the 3D camera 632 to greatly elevate the control and positioning for the robot 62 to micrometer (mm) level. As a result, the controlling system 6 of the disclosure may achieve a better control and adjustment for the endoscope 4 to lower the possibility of misjudgment from the doctor 1 in the operation.

In the disclosure, the controlling system 6 is configured to perform alignment for the 2D camera 631 and 3D camera 632 in advance. By performing pixel-to-pixel comparison to RGB image captured by the 2D camera 631 and depth image generated by the 3D camera 632, the 2D camera 631 and 3D camera 632 may achieve RGG-D registration on size and position.

In the disclosure, the controlling system 6 is configured to further control the 3D camera 632 to shoot the identified doctor 1's head to obtain the depth information. Further, the host 61 is configured to further compare the depth information to the facial feature captured by the 2D camera 631 to determine whether the facial feature and depth information are both consistent with the registered user.

As described above, the 2D camera 631 and 3D camera 632 are pre-aligned to achieve the precisely positioned state, and thus the host 61 is configured to align multiple feature points on the facial feature and depth information.

In some embodiments, the registered data 611 may record the facial features and face depth information of the registered users. In the embodiment, the host 61 is configured to determine that the doctor 1 is a specific registered user through the facial features, and compare the aligned facial features and depth information with the facial features and face depth information in the registered data 611 of the registered user to determine whether the doctor 1's face is consistent with the 3D face profile of the registered user being pre-stored.

When the facial features and depth information being captured are respectively consistent with the registered data 611 of the registered user, the host 61 may determine that the facial features and depth information are both consistent with the registered user. The aforementioned description is part of the embodiments of the disclosure, here is not intended to be limiting.

Specifically, the purpose of the controlling system 1 of the disclosure executing the primary recognition stage and secondary confirmation stage is that: (1) two independent identifying operations are executed based on the data obtained by the 2D camera 631 and 3D camera 632 to effectively exclude erroneous identification, the host 61 is prevented from erroneous identification that is caused by the similarity of the person or feature points in the environment and the registered data 611; and (2) the control and positioning to the robot 62 is greatly elevate to micrometer level through the comparison and alignment for the coordinate positions of the feature points between the image obtained by the 2D camera 631 and the image obtained by the 3D camera 632, and thereby achieving a better control and adjustment for the endoscope 4.

Further, if the host 61 identifies that the doctor 1 in front of the complex camera 63 is the registered user, and the facial features and depth information of the doctor 1 are both consistent with the registered user, the host 61 may be configured to further estimate the 2D space information and the 3D space information of the doctor 1's head according to the facial features and depth information.

In some embodiments, the complex camera 63 uses a camera coordinate system. The 2D space information includes the coordinate positions of each feature point, which is in the presently taken head image, on the x-axis and y-axis of the camera coordinate system, and the angle of each feature point on the camera coordinate system. The 3D space information includes the coordinate positions of each feature point, which is in the presently taken depth image of the head, on the x-axis, y-axis and z-axis of the camera coordinate system, and the angle of each feature point on the camera coordinate system (described hereafter).

In the disclosure, the complex camera 63 uses the camera coordinate system, and the robot 62 uses the robot coordinate system. The controlling system 6 is configured to create the transformation matrix 612 according to the corresponding relation between the camera coordinate system and robot coordinate system, and transform the 2D space information and 3D space information from the camera coordinate system to the robot moving information corresponding to the robot coordinate system by the transformation matrix. Therefore, the host 61 may be configured to directly control the robot 62 to move according to the robot moving information.

The 2D space information and 3D space information are generated based on the minor actions of the doctor 1's head, and the robot moving information is generated based on the 2D space information and 3D space information. In other words, the robot 62's movement is positive correlation with the minor actions of the doctor 1's head.

The detail of the transformation matrix 612 is omitted here for brevity.

Specifically, after the complex camera 63 of the disclosure is being disposed, the complex camera 63 has a predetermined camera coordinate system origin (0, 0, 0) on the camera coordinate system. When the robot 62 is controlled and moved to the specific position by the doctor 1 or physician assistant, the doctor 1 or physician assistant may trigger a configuration button (not shown in figures) to lock the robot 62 at the specific position, and make the specific position as the camera coordinate system origin (0, 0, 0) on the camera coordinate system for the robot 62.

In the disclosure, the host 61 is configured to create the transformation matrix 612 according to the camera coordinate system, the camera coordinate system origin, the robot coordinate system and the robot coordinate system origin. The host 61 may effectively and precisely transform the actions of the doctor 1's head, face or eye (for example, moving, yawing, rolling and pitching, etc.) to the corresponding actions of the robot 62 through the transformation matrix 612. As a result, the endoscope 4 held by the robot 62 may directly change its AOV according to the doctor 1's view, and the endoscopic image required by the doctor 1 may be precisely obtained.

Figure 4:
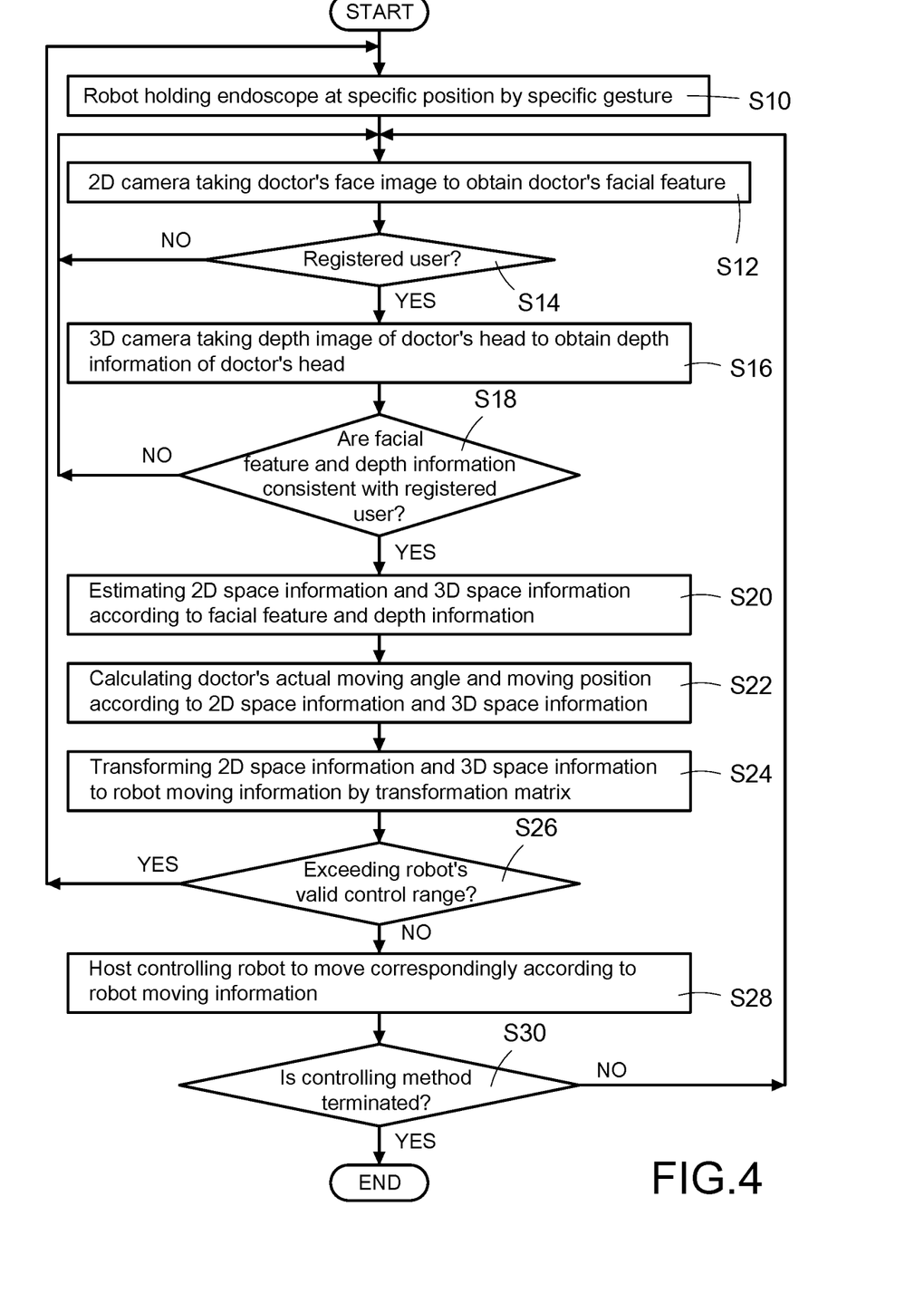
FIG. 4 is a flowchart of the controlling method in accordance with the first embodiment of the disclosure.

Please refer to FIG. 2, FIG. 3 and FIG. 4, FIG. 4 is a flowchart of the controlling method in accordance with the first embodiment of the disclosure. The disclosure further discloses a controlling method used to control an endoscopic surgical robot based on head tracking (abbreviated as the controlling method hereafter in the specification). The controlling method is mainly applied to the controlling system 6 shown in FIG. 2 and FIG. 3.

In order to apply the controlling method of the disclosure, the doctor 1 or physician assistant needs to operate the robot 62 disposed in the operating room to make the robot 62 hold the endoscope 4 used in the operating room at a specific position by a specific gesture (step S10). In some embodiments, the doctor 1 or physician assistant may drag the robot 62 manually to make the robot 62 move to the specific position and hold the endoscope 4. In some other embodiments, the doctor 1 or physician assistant may control the electronic device (not shown in figures) to output control command to make the robot 62 automatically move to the specific position and hold the endoscope 4 according to the control command. The aforementioned description is part of the embodiments of the disclosure, here is not intended to be limiting. Specifically, during the endoscopic surgery, the physician assistant needs to insert the endoscope 4 into the patient 3's body manually, and make the endoscope 4 take the image required by the doctor 1. Afterward, the doctor 1 or physician assistant may control the robot 62 to hold the endoscope 4 to replace the physician assistant. Further, the controlling system 6 is configured to set the position, where the robot 62 holds the endoscope 4, as the specific position. In the disclosure, the controlling system 6 is configured to identify the specific position as the origin of the robot 62 on the robot coordinate system, thereby generating the transformation matrix 612.

Thereafter, the controlling system 6 is configured to take the face image from the face position of the doctor 1 through the 2D camera 631 of the complex camera 63 to obtain the facial feature of the doctor 1 (step S12). Specifically, the complex camera 63 may be configured to continuously shoot toward the doctor 1's position after the operation begins. As described above, the complex camera 63 is mainly disposed above the display screen 5 in the operating room. When the doctor 1 looks up to check the display screen 5, the complex camera 63 may take the face image of the doctor 1, and the host 61 may detect the facial features of the doctor 1 in the face image. Further, since the doctor 1's face is directly facing the complex camera 63, the controlling system 6 may directly use the camera coordinate system used by the complex camera 63 to indicate the coordinate position of each feature point in the face image.

Specifically, in the step S12, the controlling system 6 is configured to take a color image of the doctor 1 by the 2D camera 631, and generate a bounding box including the face in the color image by the host 61. Afterward, the host 61 is configured to find a center point in the bounding box, and take the center point as a datum point of the doctor 1's face to align with the coordinate center point of the complex camera 63. The host 61 is configured to correlate the coordinate of the doctor 1's face and the coordinate of the complex camera 63. Therefore, the camera coordinate system used by the complex camera 63 may be used to indicate the coordinate of each feature point on the doctor 1's face.

In some embodiments, the host 61 is configured to track the doctor 1's face in the bounding box, and use the camera coordinate system to indicate the coordinate position of the face after moving. The detail is omitted here for brevity.

After the step S12, the host 61 is configured to perform identifying through the facial features to determine whether the doctor 1 in front of the complex camera 63 is the registered user (step S14). That is, the host 61 is configured to confirm whether the doctor 1 has the qualification for operating the controlling system 6.

As described above, the host 61 of the disclosure is computer host having DLA or GPU. The host 61 may have multiple registered data 611, that records the facial features of multiple doctors (that is, registered users), by pre-capturing facial features of multiple doctors to perform deep learning. In the step S14, the host 61 mainly captures the facial features of the doctor 1 from the face image taken by the 2D camera 631, and compares the facial features with the facial features of the registered users (that is, registered doctor) recorded in the registered data 611 to determine whether the doctor 1 is one of the registered users.

If the doctor 61 is determined to be not the registered user, the controlling system 6 is configured to return to the step S12 to control the 2D camera 631 to re-capture the face image of the doctor 1, and control the host 61 to re-identify.

If the doctor 61 is determined to be one of the registered users, the controlling system 6 is configured to further control the 3D camera 632 in the complex camera 63 to take the depth image from the doctor 1's head position to obtain the depth information of the doctor 1's head (step S16). Specifically, the 2D camera 631 and 3D camera 632 of the disclosure are disposed at the same position (for example, above the display screen 5) and have the same AOV (for example, toward the doctor 1's position), thereby using the same camera coordinate system.

According to the aforementioned characteristics, the operator of the controlling system 6 may execute the aforementioned aligning action to the 2D camera 631 and 3D camera 632 in advance to make the 2D camera 631 and 3D camera 632 achieve the RGB-D registration. Therefore, after the facial features are obtained from the face image taken by the 2D camera 631 and the depth information is obtained from the depth image taken by the 3D camera 632, the host 61 is configured to compare the depth information to the facial features, and determine whether the facial features and depth information are both consistent with the registered user (step S18).

If the facial features and depth information are determined to be not consistent with the registered user in the step S18, it indicates that the doctor 1 in front of the complex camera 63 may be not the registered user, or the person in front of the complex camera 63 is someone having similar features with any registered user. Under that condition, the controlling system 6 is configured to return to the step S12 to control the 2D camera 631 to re-capture the face image of the doctor 1, and control the host 61 to re-identify.

If the facial features and depth information are determined to be consistent with the registered user in the step S18, it indicates that the doctor 1 in front of the complex camera 63 passes the primary recognition stage and secondary confirmation stage. Thereafter, the host 61 is configured to respectively estimate the 2D space information and 3D space information of the doctor's head according to the facial features and depth information (step S20).

Specifically, the facial features are obtained based on the color image taken by the 2D camera 631, and the host 61 may be configured to compute the 2D space information of the doctor 61 based on the facial features. The depth information is obtained based on the depth image taken by the 3D camera 632, and the host 61 may be configured to compute the 3D space information of the doctor 61 based on the depth information. The 2D camera 631 is focus on the color and resolution (for example, 13 megapixels, 2K, or 4K etc.) of the image, and the 3D camera 632 is focus on the depth feature of each feature point in the image. Therefore, the disclosure combines the 2D space information and 3D space information to precisely calculate the moving amount of the doctor 1's head.

The host 61 is configured to calculate the actual moving angle and moving position of the doctor 1 through the 2D space information obtained in the primary recognition stage and the 3D space information obtained in the secondary confirmation stage (step S22). Further, the host 61 is configured to transform the 2D space information and 3D space information to the robot moving information by the transformation matrix 612 (step S24).

In some embodiments, the host 61 is configured to directly use the transformation matrix 612 to perform calculation to the 2D space information and 3D space information to generate the robot moving information represented by the robot coordinate system.

In some other embodiments, the host 61 is configured to calculate the actual moving angle and moving position of the doctor 1 according to the 2D space information and 3D space information. The moving angle and moving position are a moving information represented by the camera coordinate system. In the step S24, the host 61 calculate the moving information by the transformation matrix 612 to transform the moving information to the robot moving information represented by the robot coordinate system. The aforementioned description is part of the embodiments of the disclosure, here is not intended to be limiting.

Figure 5:
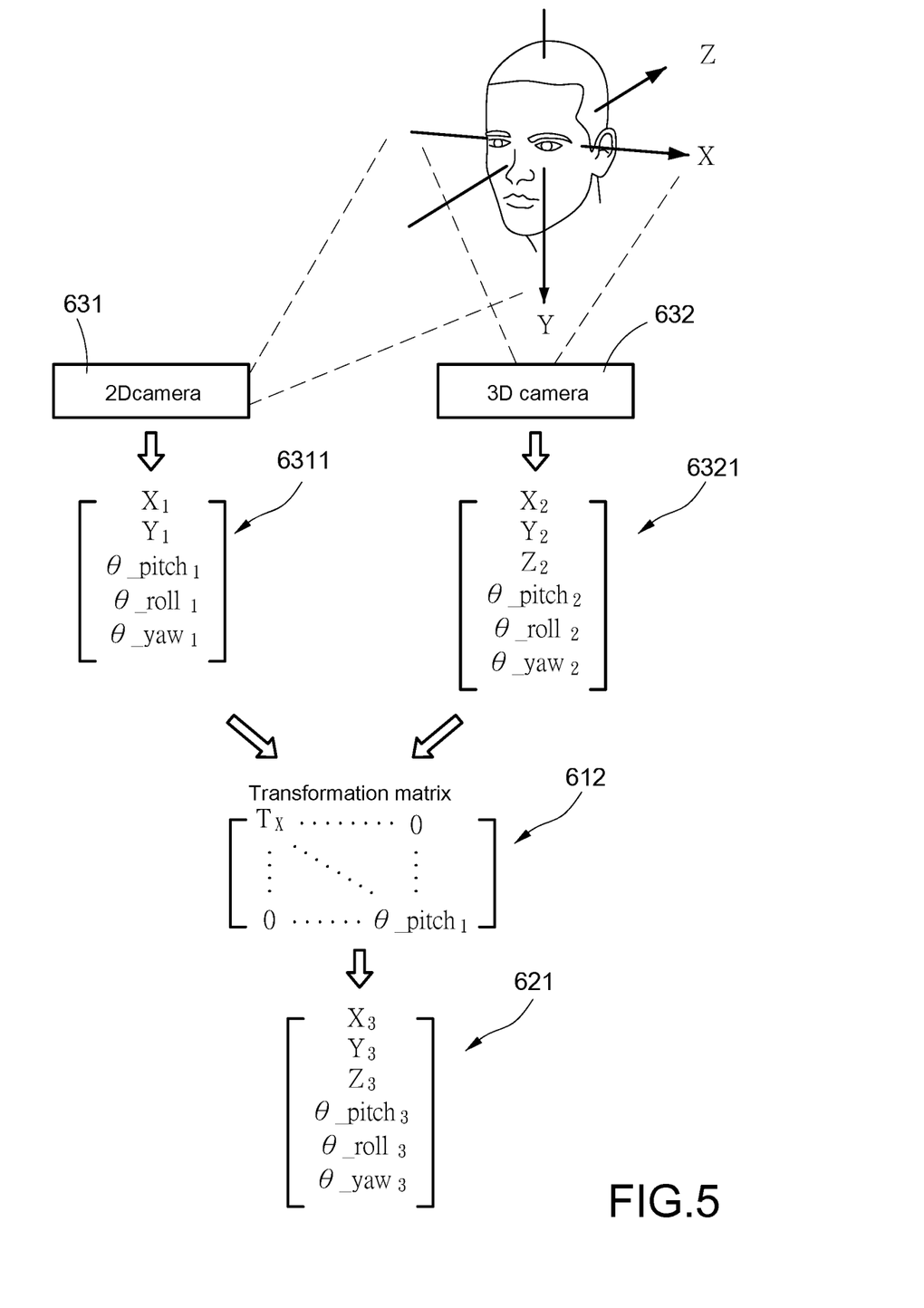
FIG. 5 is a schematic diagram of the information transformation in accordance with the first embodiment of the disclosure.

Please refer to FIG. 5, which is a schematic diagram of the information transformation in accordance with the first embodiment of the disclosure. In the step S12, the controlling system 6 is configured to take the color image of the doctor 1's face through the 2D camera 631, and generate the corresponding 2D space information 6311 after the host 61 performs analyzation and estimation to the color image. As shown in FIG. 5, the 2D space information 6311 may include, for example, the first x-axis coordinate ($X_1$), first y-axis coordinate ($Y_1$), first yaw angle ($\theta\_yaw_1$), first roll angle ($\theta\_roll_1$) and first pitch angle ($\theta\_pitch_1$) of the doctor 1's head. It is worth mentioning that the 2D space information 6311 is mainly indicated by the camera coordinate system. Further, the 2D space information 6311 is generated based on the planar color image, and thus no z-axis coordinate is included.

In the step S16, the controlling system 6 is configured to take the depth image of the doctor 1's head through the 3D camera 632, and generate the corresponding 3D space information 6321 after the host 61 perform analyzation and estimation to the depth image. As shown in FIG. 5, the 3D space information 6321 may include, for example, the second x-axis coordinate ($X_2$), second y-axis coordinate ($Y_2$), second z-axis coordinate ($Z_2$), second yaw angle ($\theta\_yaw_2$), second roll angle ($\theta\_roll_2$) and second pitch angle ($\theta\_pitch_2$) of the doctor 1's head. It is worth mentioning that the 3D space information 6321 is mainly indicated by the camera coordinate system.

In the step S24, the host 61 is configured to transform the 2D space information 6311 and 3D space information 6321 of the doctor 1 to the robot moving information 621 by the transformation matrix 612. As shown in FIG. 5, the robot moving information 621 may include, for example, the third x-axis coordinate ($X_3$), third y-axis coordinate ($Y_3$), third z-axis coordinate ($Z_3$), third yaw angle ($\theta\_yaw_3$), third roll angle ($\theta\_roll_3$) and third pitch angle ($\theta\_pitch_3$) of the robot 62. It is worth mentioning that the robot moving information 621 is mainly indicated by the robot coordinate system.

Figure 6:
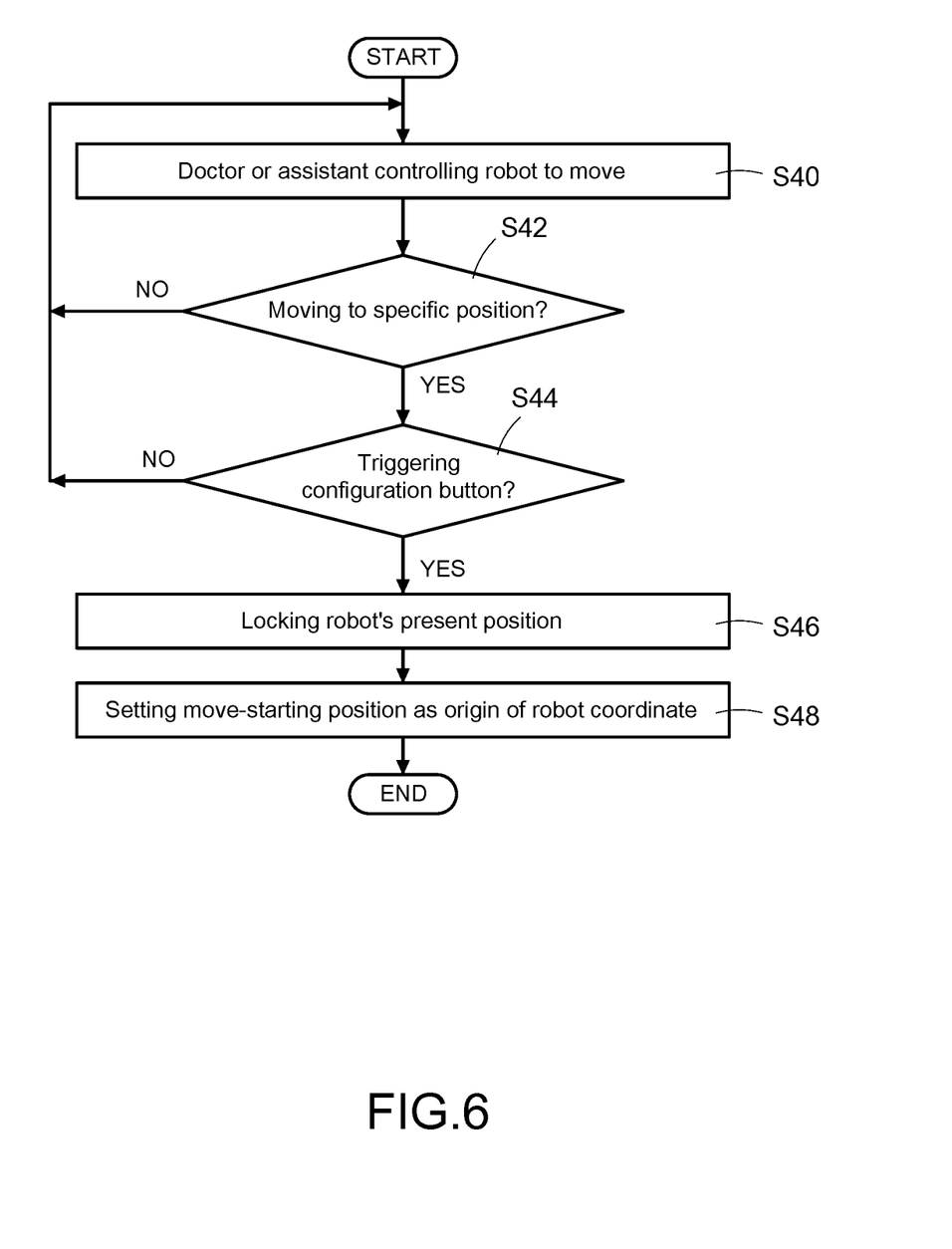
FIG. 6 is a flowchart of positioning in accordance with the first embodiment of the disclosure.

Please refer to FIG. 6, which is a flowchart of positioning in accordance with the first embodiment of the disclosure. FIG. 6 is used to further explain the step S10 in FIG. 4.

As shown in FIG. 6, in the step S10, the doctor 1 or physician assistant manually controls the robot 62 to move (step S40), and continuously determine whether the doctor 62 already moves to the specific position required by the doctor 1 (step S42). When the robot 62 is moved to the specific position, the controlling system 6 waits for the doctor 1 or physician assistant to trigger corresponding configuration button (for example, disposed on the pedal under the operation table) (step S44). When the configuration button is triggered, the controlling system 6 is configured to lock the present position of the robot 62 (step S46), and set the present position (that is, the specific position) of the robot 62 to be the move-starting position of the robot 62 on the robot coordinate system. In some embodiments, the move-starting position is set to be the robot coordinate system origin on the robot coordinate system (step S48).

Relatively, the 2D camera 631 is configured to take the face image of the doctor 1 in the step S12 of FIG. 4, when the doctor 1 looks up and faces the complex camera 63. Afterward, the controlling system 6 may be configured to use the position and angle when the doctor 1's face is directly facing the complex camera 63 to be the move-starting position of the doctor 1 on the camera coordinate system, and the move-staring position is the datum coordinate (0, 0, 0) of the doctor 1 on the camera coordinate system.

As described above, the host 61 is configured to create the transformation matrix 612 according to the camera coordinate system, the camera coordinate system origin, the robot coordinate system and the robot coordinate system origin. In the embodiment, the robot 62's position is indicated by the robot coordinate system, and the doctor 1's face position is indicated by the camera coordinate system. Therefore, the host 61 may transform the moving information of the face represented by the camera coordinate system to the robot moving information 621 represented by the robot coordinate system through the transformation matrix 612.

Referring back to FIG. 4, after the step S24, the controlling system 6 is configured to determine whether the robot moving information 621 exceeds the valid control range of the robot 62 (step S26). If the robot moving information 621 exceeds the valid control range of the robot 62, the controlling system 6 is configured to return to the step S10 for the doctor 1 or physician assistant to adjust the position of the robot 62 or endoscope 4.

Specifically, if the robot moving information 621 exceeds the valid control range of the robot 62, it represents that the movement of the doctor 1's head is over range, or the present position of the robot 62 or endoscope 4 is not consistent with the doctor 1's requirement. Under that condition, the controlling system 6 is configured to not control the robot 62 according to the robot moving information 621 directly to reduce the possibility of misjudgment.

In contrary, if the robot moving information 621 is determined to be not exceeding the valid control range of the robot 62 in the step S26, the controlling system 6 is configured to control the robot 62 to move correspondingly according to the robot moving information 621 (step S28). The movement of the robot 62 may drive the AOV of the endoscope 4 for corresponding adjustment. The robot moving information 621 is generated based on the movement of the doctor 1's face, and thus AOV of the endoscope 4 may be adjusted following the moving of the doctor 1's face to obtain the image required by the doctor 1.

After the step S28, the controlling system 6 is configured to determine whether the controlling method is terminated (step S30). If the controlling method is not terminated (for example, the operation is not terminated, the controlling system 6 is not closed yet, etc.), the controlling system 6 is configured to return to the step S12 and execute the step S12 to step S28 repeatedly. Therefore, the controlling system 6 may continuously track the movement of the doctor 1's face to control the robot 62 correspondingly (that is, correspondingly adjusting AOV of the endoscope 4 to assist the operation to be performed smoothly), before the operation of the doctor 1 is completed.

In order to further lower the possibility of misjudgment, apart from executing the secondary confirmation stage through the 3D camera 632, the controlling system 6 of the disclosure may be configured to determine whether the doctor 1 has practical control intension through supplementary manner. In some embodiments, the controlling system 6 is configured to execute the controlling method of the disclosure, when the doctor 1 is determined to be having control intension, to make the doctor 1 has the authority of directly controlling the robot 62 and/or endoscope 4 by face actions.

Figure 7:
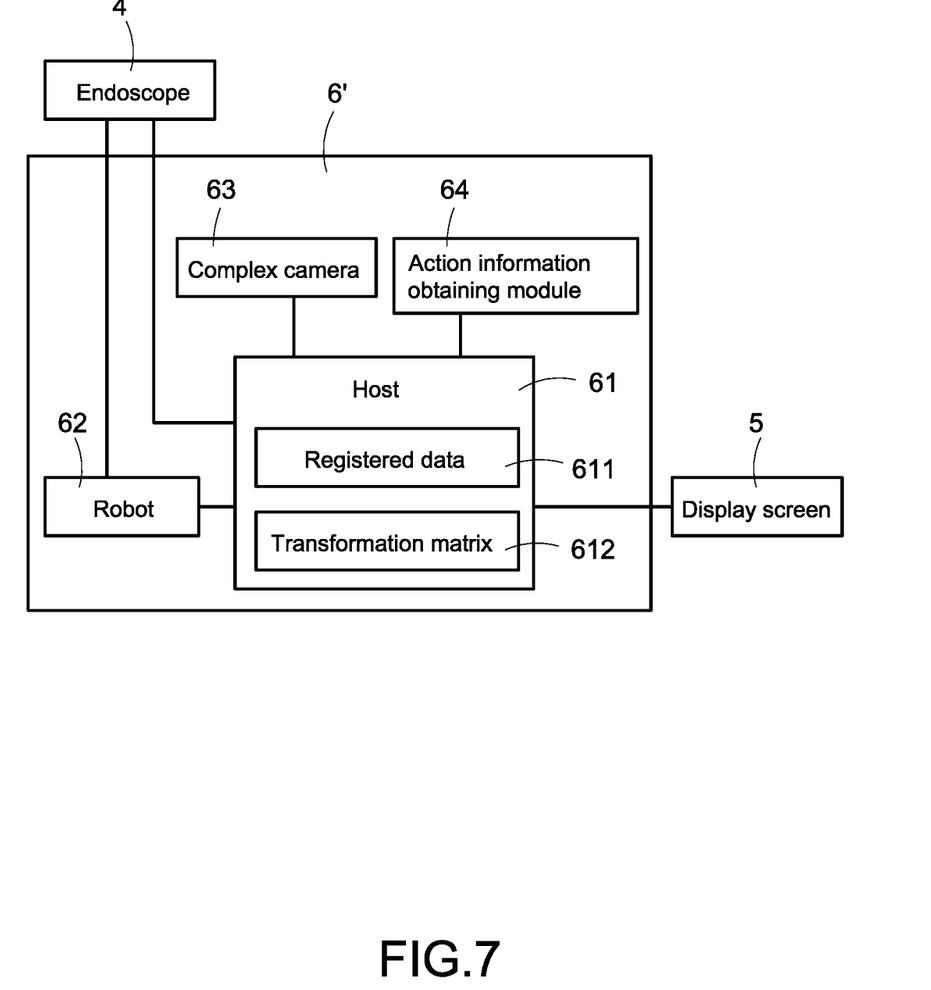
FIG. 7 is a block diagram of the controlling system in accordance with the second embodiment of the disclosure.
Figure 8:
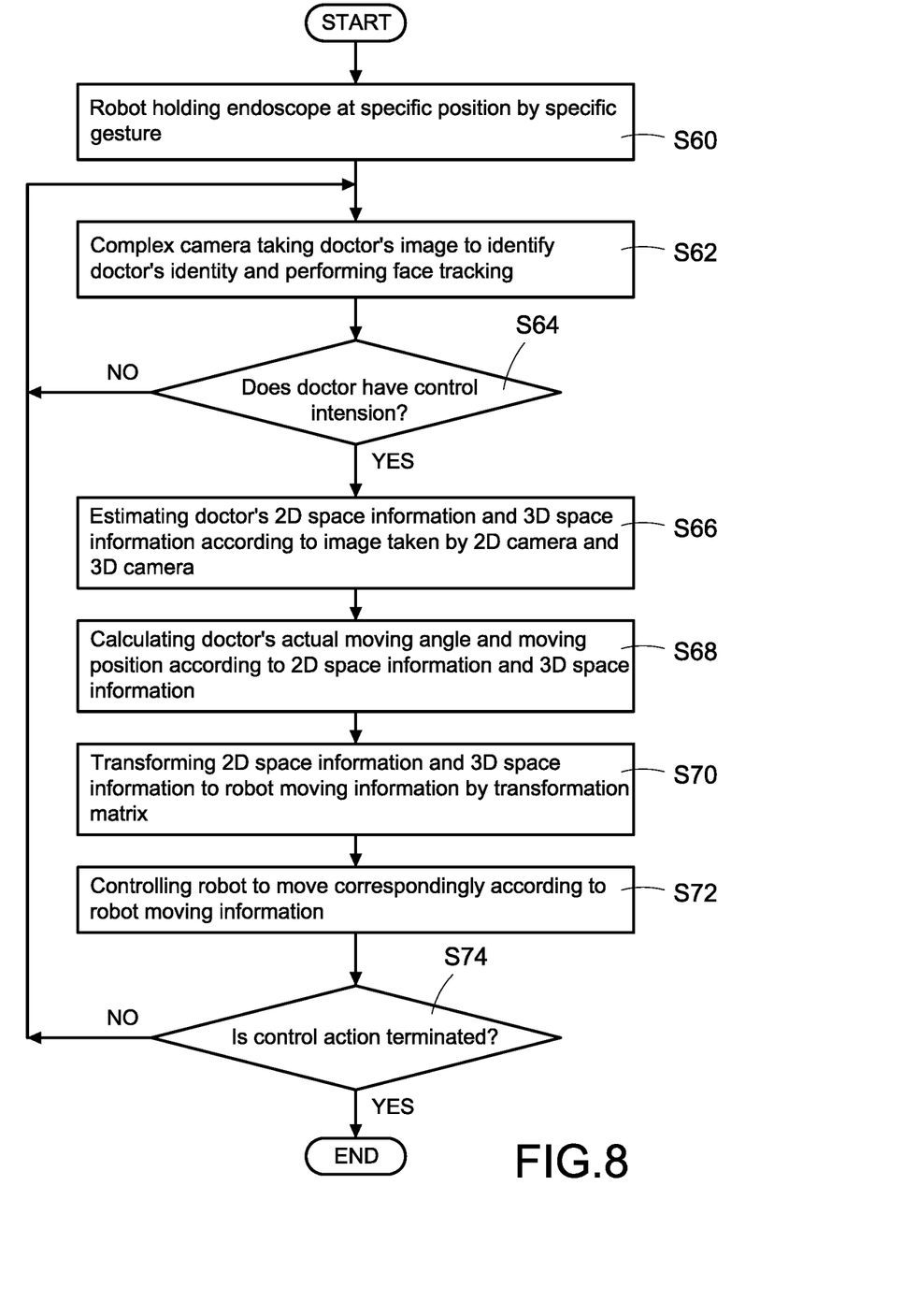
FIG. 8 is a flowchart of the controlling method in accordance with the second embodiment of the disclosure.

Please refer to FIG. 7 and FIG. 8, FIG. 7 is a block diagram of the controlling system in accordance with the second embodiment of the disclosure, FIG. 8 is a flowchart of the controlling method in accordance with the second embodiment of the disclosure.

FIG. 7 discloses the controlling system 6' of another embodiment in the disclosure. Specifically, the controlling system 6' includes the host 61, robot 62 and complex camera 63 similar to the aforementioned controlling system 6, and the detail is omitted here for brevity.

The difference between the controlling system 6' and controlling system 6 is that the controlling system 6' further includes an action information obtaining module 64 connected with the host 61. In some embodiments, the action information obtaining module 64 is used for detecting whether the doctor 1 has the control intension to the robot 62 and/or endoscope 4, and outputting corresponding confirmation signal when the doctor 1 indeed has the control intension. It should be noted that the control intension may include the intension of activating, urgently stopping, or braking the robot 62 and/or endoscope 4. In other words, the action information obtaining module 64 is configured to output the confirmation signal corresponding to the specific intension.

In some embodiments, the action information obtaining module 64 may be a voice control module. The controlling system 6' is configured to determine that the doctor 1 had the control intension, when the voice control module receives the voice control command from the doctor 1.

In some embodiments, the action information obtaining module 64 may be a pedal disposed under the operation table. The controlling system 6' is configured to determine that the doctor 1 had the control intension, when the doctor 1 treads the pedal during the operation.

In some embodiments, the action information obtaining module 64 may be a button disposed on any position. The controlling system 6' is configured to determine that the doctor 1 had the control intension, when the doctor 1 pushes the button during the operation.

In some embodiments, the action information obtaining module 64 may be an eye tracking camera (for example, miniature macro camera) worn on the doctor 1's head. The eye tracking camera is configured to continuously track the doctor 1's view and eyeball through image recognition technology. When the eye tracking camera detects that the doctor 1's view focus on the endoscopic image displayed on the display screen 5, the controlling system 6' is configured to determine that the doctor 1 has the control intension.

The aforementioned description is part of the embodiments of the disclosure, here is not intended to be limiting.

As shown in FIG. 8, during the operation, the doctor 1 or physician assistant controls the robot 62 to make the robot 62 hold the endoscope 4 at the specific position by the specific gesture (step S60). Thereafter, the controlling system 6' is configured to take the image of the doctor 1 through the 2D camera 631 and 3D camera 632 on the complex camera 63, and identify the doctor 1's identity through the image and perform face tracking (step S62).

Afterward, the controlling system 6' is configured to determine whether the doctor 1 has control intension through the action information obtaining module 64 (step S64). If the doctor 1 is determined to be having control intension in the step S64, the action information obtaining module 64 is configured to transmit corresponding confirmation signal to the host 61. After the confirmation signal is received, the host 61 may execute the steps shown in FIG. 4 to track the actions on the doctor 1's face and control the robot 62 correspondingly.

Specifically, after the confirmation signal output by the action information obtaining module 64 is received, the host 61 may be configured to estimate the 2D space information 6311 and 3D space information 6321 according to the images taken by the 2D camera 631 and 3D camera 632 (step S66), and compute the actual moving angle and moving position of the doctor 1 according to the 2D space information 6311 and 3D space information 6321 (step S68). Afterward, the host 61 is configured to transform the 2D space information 6311 and 3D space information 6321 to the robot moving information 621 by the transformation matrix 612 (step S70), and control the robot 62 to move correspondingly according to the robot moving information 621 (step S72). The robot 62 is controlled to move through changing of the doctor 1's view, and further drive the endoscope 4 held by the robot 62 to adjust correspondingly, thereby achieving consistence between AOV of the endoscope 4 and the doctor 1's view.

After the step S72, the host 61 is configured to determine whether the control action from the doctor 1 is terminated (step S74), and execute the step S62 to step S72 repeatedly before the control action is terminated to continuously track the actions of the doctor 1's face, and control the robot 62 to move based on the actions of the doctor 1's face to continuously adjust AOV of the endoscope 4.

As described above, the disclosure is used to make the system directly adjust AOV of the endoscope according to changing of the doctor's view, and make the image captured by the endoscope be more consistent with the practical requirement from the doctor. As a result, the disclosure may reduce the reliance to manpower, such as the physician assistant, in the operation, and make the control of the endoscope be intuitive for the doctor.

While this disclosure has been described by means of specific embodiments, numerous modifications and variations may be made thereto by those skilled in the art without departing from the scope and spirit of this disclosure set forth in the claims.

What is claimed is:

1. A controlling system, configured to control an endoscopic surgical robot based on head tracking, applied in an operating room, the controlling system comprising:
    a host;
    a robot, connected with the host and configured to hold an endoscope used in the operating room at a specific position by a specific gesture; and
    a complex camera, comprising a 2D camera and a 3D camera, the 2D camera configured to obtain a facial feature of a doctor in the operating room, and the 3D camera configured to obtain a depth information of the doctor's head, wherein the 2D camera and the 3D camera achieve an RGB-D registration through pre-alignment;
    wherein the host is configured to identify the facial feature to determine whether the doctor is a registered user, and compare the depth information to the facial feature to determine whether the facial feature and the depth information are both consistent with the registered user, when the doctor is determined to be the registered user and the facial feature and the depth information are determined to be consistent with the registered user, the host is configured to estimate a 2D space information and a 3D space information of the doctor's head according to the facial feature and the depth information, transform the 2D space information and the 3D space information to a robot moving information by a transformation matrix, and control the robot to move according to the robot moving information.

2. The controlling system according to claim 1, wherein the host is configured to store multiple registered data, each registered data records the facial feature of at least one registered user, and the host is configured to compare the facial feature with the multiple registered data to identify the doctor is one of multiple registered users.

3. The controlling system according to claim 1, wherein the host is connected with the endoscope and a display screen in the operating room to transmit image of the endoscope to display on the display screen, and the complex camera is disposed above the display screen.

4. The controlling system according to claim 1, wherein the 2D camera supports RGB color image, and the 3D camera is configured to capture and generate the depth information through a time-of-flight (ToF) technology, a stereoscopy technology or s structure light technology.

5. The controlling system according to claim 1, wherein the 2D space information comprises a first x-axis coordinate, a first y-axis coordinate, a first yaw angle, a first roll angle and a first pitch angle of the doctor's head, the 3D space information comprises a second x-axis coordinate, a second y-axis coordinate, a second yaw angle, a second roll angle and a second pitch angle of the doctor's head, and the robot moving information comprises a third x-axis coordinate, a third y-axis coordinate, a third yaw angle, a third roll angle and a third pitch angle of the robot.

6. The controlling system according to claim 1, wherein the complex camera is configured to use a camera coordinate system with a camera coordinate system origin, the robot is configured to use a robot coordinate system with a robot coordinate system origin of the specific position, and the host is configured to create the transformation matrix according to the camera coordinate system, the camera coordinate system origin, the robot coordinate system and the robot coordinate system origin.

7. The controlling system according to claim 1, further comprising:
    an action information obtaining module, connected with the host,
    wherein the host is configured to calculate the robot moving information when receiving a confirmation signal transmitted by the action information obtaining module.

8. The controlling system according to claim 7, wherein the action information obtaining module comprises a voice control module, a pedal, a button or an eyeball tracking camera worn on the doctor's head.

9. A controlling method, used to control an endoscopic surgical robot based on head tracking, applied to a controlling system comprising a robot, a complex camera and a host, the controlling method comprising:

a) controlling the robot to hold an endoscope used in an operating room at a specific position by a specific gesture;

b) obtaining, by a 2D camera in the complex camera, a facial feature of a doctor in the operating room;

c) identifying, by the host, the facial feature to determine whether the doctor is a registered user;

d) obtaining, by a 3D camera in the complex camera, a depth information of the doctor's head, wherein the 2D camera and the 3D camera achieve an RGB-D registration through pre-alignment;

e) comparing, by the host, the depth information to the facial feature to determine whether the facial feature and the depth information are both consistent with the registered user;

f) when the doctor is determined to be the registered user and the facial feature and the depth information are determined to be consistent with the registered user, estimating, by the host, a 2D space information and a 3D space information of the doctor's head according to the facial feature and the depth information;

g) transforming, by the host, the 2D space information and the 3D space information to a robot moving information by a transformation matrix; and h) controlling, by the host, the robot to move according to the robot moving information.

10. The controlling method according to claim 9, further comprising:

displaying image of the endoscope on a display screen in the operating room, wherein the complex camera is disposed above the display screen, the 2D camera supports RGB color image, and the 3D camera is configured to capture and generate the depth information through a time-of-flight (ToF) technology or s structure light technology.

11. The controlling method according to claim 9, wherein the c) further comprising:

comparing the facial feature with multiple registered data; wherein each registered data records the facial feature of at least one registered user.

12. The controlling method according to claim 9, wherein the 2D space information comprises a first x-axis coordinate, a first y-axis coordinate, a first yaw angle, a first roll angle and a first pitch angle of the doctor's head, the 3D space information comprises a second x-axis coordinate, a second y-axis coordinate, a second yaw angle, a second roll angle and a second pitch angle of the doctor's head, and the robot moving information comprises a third x-axis coordinate, a third y-axis coordinate, a third yaw angle, a third roll angle and a third pitch angle of the robot.

13. The controlling method according to claim 9, wherein before the a), the method further comprises:

a01) controlling the robot to move;

a02) continuously executing the a01) before the robot moves to the specific position;

a03) triggering a configuration button to lock the robot's position when the robot moves to the specific position;

a04) after the a03), setting robot's present position to be a robot coordinate system origin, wherein the complex camera is configured to use a camera coordinate system with a camera coordinate system origin, the robot is configured to use a robot coordinate system, and the host is configured to create the transformation matrix according to the camera coordinate system, the camera coordinate system origin, the robot coordinate system and the robot coordinate system origin.

14. The controlling method according to claim 9, further comprising:

g1) after the g), determining whether the robot moving information exceeds a valid control range of the robot;

g2) re-executing the a), when the robot moving information exceeds the valid control range;

g3) executing the h), when the robot moving information does not exceed the valid control range.

15. The controlling method according to claim 9, wherein the controlling system further comprises an action information obtaining module, and the controlling method further comprises:

a1) determining, by the host, whether a confirmation signal transmitted by the action information obtaining module is received; and a2) executing the f) to the h), when the confirmation signal is received.

* * * * *